US012186508B2

(12) United States Patent
Bean et al.

(10) Patent No.: US 12,186,508 B2
(45) Date of Patent: Jan. 7, 2025

(54) PATIENT SPECIFIC MEDICAL BALLOON FORMING MACHINE AND SYSTEM

(71) Applicants: THE BOARD OF TRUSTEES OF THE UNIVERSITY OF ARKANSAS, Little Rock, AR (US); BIOVENTURES, LLC, Little Rock, AR (US)

(72) Inventors: Maxwell Bean, Fayetteville, AR (US); Morten Jensen, Fayetteville, AR (US); Barry Uretsky, Little Rock, AR (US); Kaitlyn Elmer, Fayetteville, AR (US)

(73) Assignees: THE BOARD OF TRUSTEES OF THE UNIVERSITY OF ARKANSAS, Little Rock, AR (US); BIOVENTURES, LLC, Little Rock, AR (US)

(*) Notice: Subject to any disclaimer, the term of this patent is extended or adjusted under 35 U.S.C. 154(b) by 35 days.

(21) Appl. No.: 17/720,514

(22) Filed: Apr. 14, 2022

(65) Prior Publication Data
US 2022/0331565 A1 Oct. 20, 2022

Related U.S. Application Data

(60) Provisional application No. 63/174,708, filed on Apr. 14, 2021.

(51) Int. Cl.
*A61M 25/10* (2013.01)
*A61F 2/95* (2013.01)
(Continued)

(52) U.S. Cl.
CPC ......... *A61M 25/1029* (2013.01); *A61F 2/954* (2013.01); *A61F 2/958* (2013.01); *B29L 2031/7543* (2013.01); *B33Y 80/00* (2014.12)

(58) Field of Classification Search
CPC ........ A61M 25/1029; B29L 2031/7543; B29C 33/306; B29C 2049/4858
See application file for complete search history.

(56) References Cited

U.S. PATENT DOCUMENTS 5,017,325 A * 5/1991 Jackowski ........ A61M 25/1029
425/530
5,879,369 A * 3/1999 Ishida ..................... B29C 55/26
606/192
(Continued)

FOREIGN PATENT DOCUMENTS

CN 207643678 U * 7/2018
JP 4880681 B2 * 2/2012 ............... A61B 5/24
WO WO-2020038801 A1 * 2/2020 ........ A61M 25/1029

OTHER PUBLICATIONS

Machine translation of JP 4880681 B2 dated Feb. 2012. (Year: 2012).*

(Continued)

*Primary Examiner* — Robert B Davis
(74) *Attorney, Agent, or Firm* — Quarles & Brady, LLP

(57) ABSTRACT

Patient specific medical balloons, assemblies, and systems for forming the same, and devices and methods for treating patients in need of a percutaneous coronary intervention (PCI) are disclosed. The assembly for forming the medical balloon comprises a form for receiving a parison where the form is configured to prepare a patient specific medical balloon matched in geometry to a blood vessel or a lesion for a patient in need of a PCI.

6 Claims, 6 Drawing Sheets

(51) Int. Cl.
  *A61F 2/954* (2013.01)
  *A61F 2/958* (2013.01)
  *B29L 31/00* (2006.01)
  *B33Y 80/00* (2015.01)

(56) References Cited

U.S. PATENT DOCUMENTS

| | | | |
|---|---|---|---|
| 5,948,345 A | 9/1999 | Patel et al. | |
| 6,561,788 B1* | 5/2003 | Gaudoin | B29C 49/48 |
| | | | 249/102 |
| 6,946,092 B1 | 9/2005 | Bertolino et al. | |
| 8,012,402 B2* | 9/2011 | Kleiner | B29C 35/0805 |
| | | | 264/528 |
| 8,900,207 B2 | 12/2014 | Uretsky | |
| 9,844,651 B2* | 12/2017 | Maeda | B29C 49/22 |
| 2007/0267780 A1* | 11/2007 | Schewe | B29C 33/42 |
| | | | 264/300 |
| 2010/0057020 A1* | 3/2010 | Uretsky | A61F 2/954 |
| | | | 604/533 |
| 2010/0323048 A1* | 12/2010 | Donlon | A61M 16/0445 |
| | | | 128/207.15 |
| 2015/0105770 A1* | 4/2015 | Amit | A61B 18/1492 |
| | | | 606/41 |
| 2019/0046270 A1* | 2/2019 | Belson | A61B 34/10 |
| 2021/0259777 A1* | 8/2021 | Chatzizisis | A61B 34/10 |

OTHER PUBLICATIONS

Chen, Y. Modeling and cycle-to-cycle control of the angioplasty balloon forming process. (McGill University (Canada), 2008).
Louvard, Y. et al. Classification of coronary artery bifurcation lesions and treatments: Time for a consensus! Catheterization and Cardiovascular Interventions 71, 175-183 (2008).
Margo, M. et al. Acute procedural and six-month clinical outcome in patients treated with a dedicated bifurcation stent for left main stem disease: the TRYTON LM multicentre registry. Eurointervention Journal 8, (2013).
Menary, G., & Armstrong, C. (2006). Experimental study and numerical modelling of injection stretch blow moulding of angioplasty balloons. Plastics, Rubber and Composites: Macromolecular Engineering, 35(8)(8), 348-354. https://doi.org/10.1179/174328906X143877.
Timmins, L. H., Miller, M. W., Clubb Jr, F. J. & Moore Jr, J. E. Increased artery wall stress post-stenting leads to greater intimal thickening. Laboratory Investigation 91, 955-967 (2011).

* cited by examiner

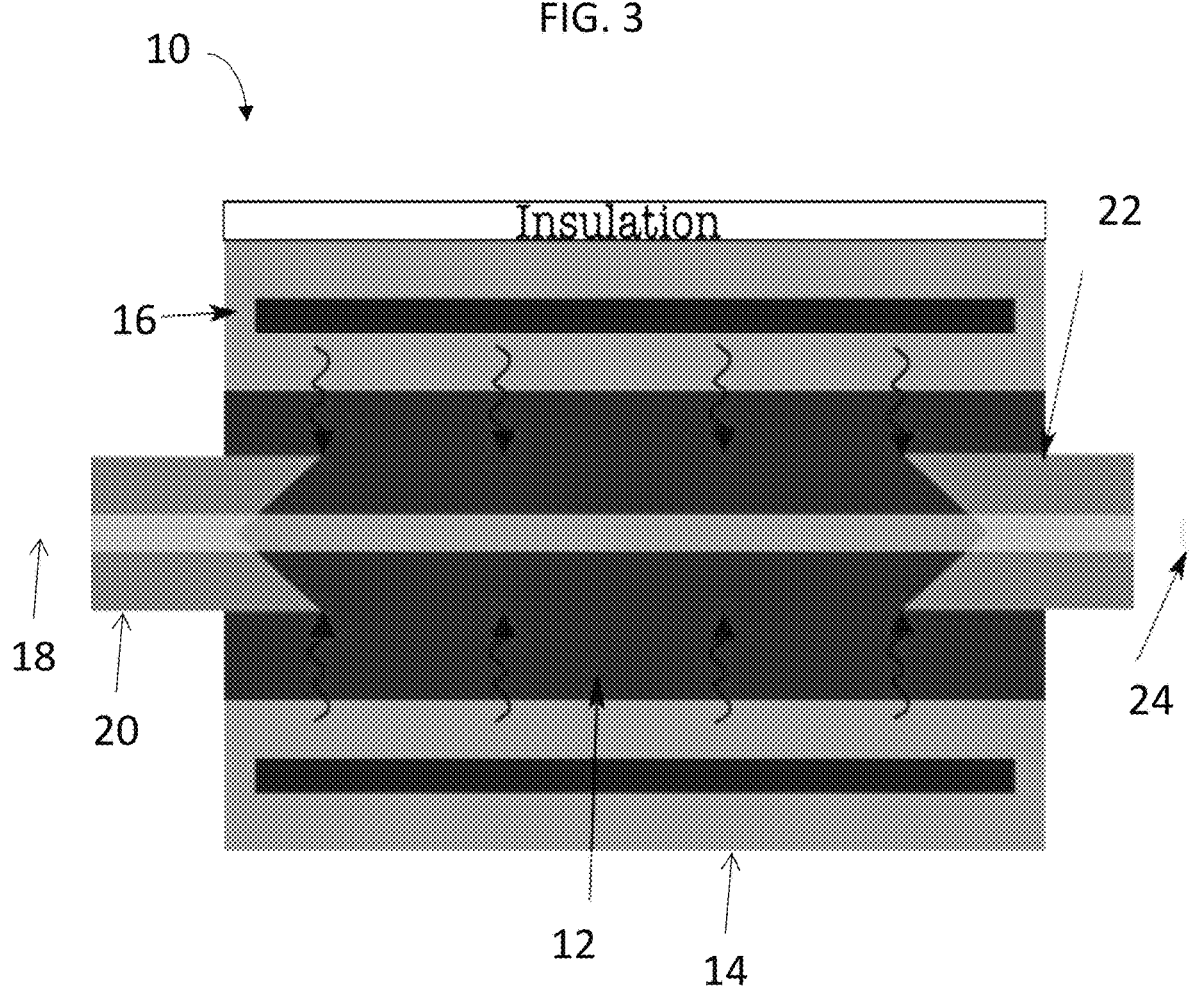

PATIENT SPECIFIC MEDICAL BALLOON FORMING MACHINE AND SYSTEM

CROSS-REFERENCE TO RELATED APPLICATION

This application claims benefit of priority to U.S. Patent Application Ser. No. 62/174,708, filed Apr. 14, 2021, the contents of which is incorporated by reference in its entirety.

BACKGROUND OF THE INVENTION

Current coronary artery stenting techniques are not designed for bifurcation lesions, which account for 15-20% of all percutaneous coronary interventions (PCI). Interventional treatment of these anatomic regions is technically challenging and can lead to adverse blood flow and tissue stress fields that can predispose the patient to restenosis of the diseased vessel and/or local thrombosis. As a result, stent placement in the bifurcation can lead to a regrowth of cells blocking the artery again or the poor placement alters blood flow enough to allow clots to form.

Usually stents are deployed in one of a number of different methodologies including: Stent+PTCA, T stenting, reverse-T, Cullotte, Y, Crush, reverse crush, minicrash, modified T or Kissing with Crush or Cullote being the foremost. These numerous techniques can create overlapping stents, which may promote restenosis, or expose a location of no stent coverage, or damage parts of one or more of the stents, also promoting restenosis. Some of these problems may be overcome by using a tapered balloon where the main branch is treated with the tapered balloon and stent followed by two smaller stents in the daughter branches, such as described in U.S. Pat. No. 8,900,207.

Bifurcation lesions, particularly in the coronary arteries, are challenging to treat percutaneously because each bifurcation lesion has a fingerprint-like uniqueness. Current balloon forming systems rely on glass forms or copper alloy forms that are expensive and time consuming to prepare. Because of the reliance on glass and metal alloy form, these systems employ a one-size-fits all approach as the balloon dimensions are governed by the mold. However, each patient has a unique configuration of blood vessels and plaque buildup configuration. Creating unique balloon designs for treatment in this area is costly and inefficient with current balloon forming technologies. As a result, there is the need for methods for designing and fabricating custom, patient specific balloon molds.

BRIEF SUMMARY OF THE INVENTION

Patient specific medical balloons, assemblies, and systems for forming the same, and devices and methods for treating patients in need of a percutaneous coronary intervention (PCI) are disclosed. One aspect of the technology is an assembly for forming a medical balloon where the assembly comprises a form for receiving a parison, wherein the form is configured to prepare a patient specific medical balloon matched in geometry to a blood vessel or a lesion therein of a patient in need of a percutaneous coronary intervention (PCI) in the blood vessel; a heated jaw configured to surround the form and heat the parison within the form to a balloon forming temperature, wherein the heated jaw is thermally coupled to a heating element; a conduit configured to provide a balloon forming medium for expanding the parison within the form; wherein the conduit is fluidly connected to a pressurizing system for pressurizing the balloon forming medium; a tensioning device configured to apply tension to the parison within the form; and optionally one or more controllers configured to control the heating element, the pressurizing system, or the tensioning device.

Another aspect of the technology is a system for forming a medical balloon where the system comprises any of the assemblies for forming a medical balloon described herein; a biometric data acquisition device, the biometric data acquisition device configured to obtain biometric data from the subject in need of the PCI of the blood vessel; a processing device, the processing device comprising a processor and memory storing instructions that, when executed by the processor, will cause the processing device to determine the form configured to prepare the patient specific medical balloon matched in geometry to the blood vessel or a lesion therein; and a forming device configured to form the form determined by the processing device.

Another aspect of the technology is a method for preparing a form configured to prepare a patient specific medical balloon where the method comprises obtaining, with a biometric data acquisition device, biometric data from a subject in need of a PCI of a blood vessel; determining, from said biometric data with a processing device, a form configured to prepare the patient specific medical balloon matched in geometry to the blood vessel or a lesion therein of the subject in need of the PCI; and forming, with a forming apparatus, the form configured to prepare the patient specific medical balloon.

Another aspect of the invention is a method for forming a patient specific medical balloon where the method comprises providing any of the assemblies for forming a medical balloon described herein; positioning the parison within the form; and expanding the parison within the form under balloon forming conditions. The method may further comprise obtaining, with a biometric data acquisition device, biometric data from a subject in need of a PCI of a blood vessel; determining, from said biometric data with a processing device, a form configured to prepare the patient specific medical balloon matched in geometry to the blood vessel or a lesion therein of the subject in need of the PCI; and forming, with a forming apparatus, the form configured to prepare the patient specific medical balloon.

Another aspect of the technology is a method for preparing a balloon catheter device for use in a PCI where the method comprises attaching any of the patient specific medical balloon described herein to a catheter suitable for use in the PCI. Suitably, the patient specific medical balloon may be prepared from any of the methods described herein.

Another aspect of the technology is a method for treating a subject in need of a PCI where the method comprises locating within the subject in need of the PCI a lesion in a blood vessel having a plaque or an occlusion associated therewith; positioning a patient specific medical balloon matched in geometry to the blood vessel proximate to the lesion; and expanding the patient specific medical balloon to a matched diameter of the blood vessel to reconfigure the plaque or the occlusion within the blood vessel.

Another aspect of the technology is a method for forming a tapered parison comprising providing any of the assemblies described herein; positioning a first portion of a parison within the form and coupling a first end and a second end of the parison to the tensioning device wherein the first end extends from the form; heating, with the heated jaw surrounding the form, the first portion of the straight parison; tensioning, with the tensioning device, the heated parison; and cooling the parison under tension. In some embodiments, the method further comprises positioning a second portion of the cooled parison within the form and coupling the first end and the second end of the parison to the tensioning device, wherein the coupling of the first end and the second end is reversed from the coupling prior to tensioning and heating; heating, with the heated jaw surrounding the form, the second portion of the straight parison; tensioning, with the tensioning device, the heated parison; and cooling the parison under tension. In some embodiments, the parison having the first portion positioned within the form has straight walls. In some embodiments, the tapered parison prepared by any of the methods described herein is used in a method for preparing a patient specific medical balloon.

These and other aspects of the invention are further described herein.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIG. 3 illustrates an assembly according to the presently disclosed technology.

DETAILED DESCRIPTION OF THE INVENTION

Figure 1:
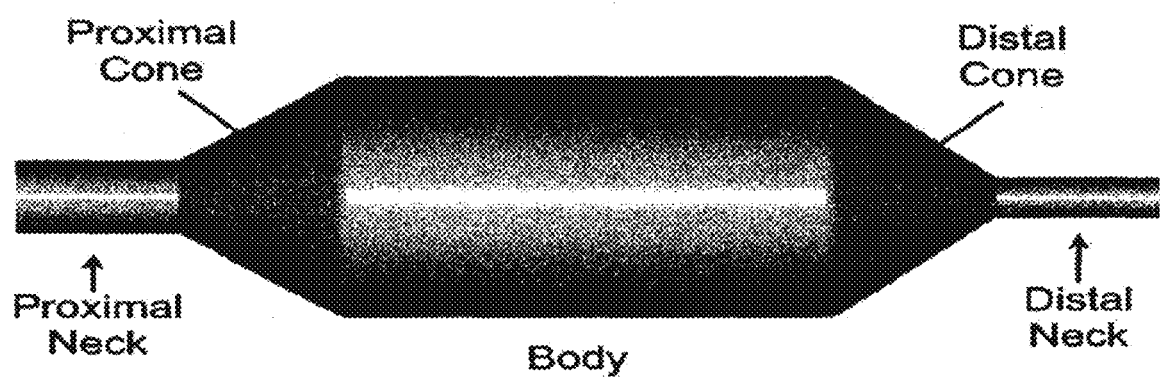
FIG. 1 illustrates a medical balloon.

Disclosed herein are patient specific medical balloons, machines, and systems for forming the same. Also disclosed herein are devices and methods for treating patients in need of a percutaneous coronary intervention (PCI). As further disclosed, forms specific for the patent may be prepared from an additive manufacturing process, such as three-dimensional (3D) printing by stereolithography, that can be used to prepare medical balloons matched to the geometry of the patient's blood vessel and/or lesion. By allowing the mold to be prepared by an additive manufacturing process, the form can be interchanged within an assembly for preparing the medical balloon. This allows for a medical balloon specific for the patient to be created in a matter of hours for a fraction of the cost of current custom balloon creation.

The patient specific medical balloons can be matched to patient's blood vessel or lesion geometry by obtaining geometries from medical imaging modalities, such as 3D cardiac CT, MRI or ultrasound. Once this biometric geometry data is obtained, a form can be prepared that allows for the medical balloon to be customized for the patient. Because expandable stents adhere to the shape of the patient specific balloon once inflated, there is no need for the stent to be custom formed as well. The use of patient specific medical balloons reduces the risk of adverse blood flow and tissue stress fields that can predispose the patient to restenosis of the diseased vessel and/or local thrombosis, resulting in improved therapeutic outcomes. As a result, the technology disclosed herein advances the field by allowing for the rapid creation of medical balloons that are the correct dimension for an individual patient's lesion.

A medical balloon is an inflatable device comprised of an extendable member that can be inserted into a body cavity or structure of a subject and distended with a gas or fluid for a therapeutic purpose, such as angioplasty. Angioplasty balloons are used to treat atherosclerosis or blockage in the arteries. For bifurcation lesions, meaning blockages in the artery bifurcations, interventions have up to a 30% higher risk of complication than a routine intervention where no bifurcations are present. Medical angioplasty balloons, such as those described in U.S. Pat. No. 8,900,207 to Barry F. Uretsky, which is incorporated herein by reference, may be used to optimally open the artery, helping guide the balloons and stents in alignment to reduce overlap or gaps.

The present technology further improves on the therapeutic outcome following percutaneous coronary intervention (PCI) by using interchangeable parts that allow patient specific medical balloons to be prepared and used for therapeutic intervention. This will allow for the rapid manufacture of patient specific balloons for any necessary procedure. The creation of custom balloons tailored specifically for the patient's blood vessel geometry will allow for the most open pathways possible while minimizing risks of failure. Just a small increase in diameter can lead to a large increase in blood flow, improving the therapeutic outcome following PCI.

Methods for treating a subject in need of a PCI are provided. PCI is a surgical procedure used to treat the narrowing of blood vessels, such as coronary arteries of the heart. The intervention typically involves angioplasty in combination with stenting to widen narrowed or obstructed blood vessels having a lesion, such as a plaque or occlusion. Bifurcation lesions in the coronary arteries or peripheral vasculature, such as in the legs, are challenging to treat percutaneously because each bifurcation lesion has a fingerprint-like uniqueness. As a result, there is a need for patient specific medical balloons that allow for optimal intervention with the patient.

Suitably, the method of treating a subject in need of a PCI may comprise locating within the subject in need of the PCI a lesion in a blood vessel having a plaque or an occlusion associated therewith, positioning a patient specific medical balloon matched in geometry to the blood vessel proximate to the lesion, and expanding the patient specific medical balloon to a matched diameter of the blood vessel to reconfigure the plaque or the occlusion within the blood vessel. In some embodiments, the method may further comprise positioning an expandable wire stent proximate to the reconfigured plaque or occlusion and expanding the expandable wire stent with the patient specific medical balloon. Suitably, the lesion may be a bifurcation lesion but it need not be. Accordingly, the patient specific medical balloon is positioned in a main branch area or distal to a carina prior to expansion. Methods for treating patients needing a PCI are provided for in U.S. Pat. No. 8,900,207.

As used herein, a "patient" may be interchangeable with "subject" or "individual" and means an animal, which may be a human or non-human animal, in need of treatment. A "patient in need of treatment" may include a subject having a disease, disorder, or condition that is responsive to therapy to treat the narrowing of blood vessels. For example, a "patient in need of treatment" may include a subject in need of treatment to prevent or reverse coronary artery disease, atherosclerosis, vascular occlusion, myocardial infarction, or angina.

As used herein, a "patient specific medical balloon" is a medical balloon sized to match the geometry of the patient's blood vessel and/or lesion within the blood vessel. Accordingly, the patient specific medical balloon may have one or more geometric parameters that are determined as a result of obtaining biometric data from the patient in need of a PCI. The geometric parameters may determine the patient specific medical balloons maximum expandable body diameter, a radius of curvature, a taper, a length of the body, a cylindrical portion, a proximal or distal cone geometry, or any other suitably selected geometric parameter of the medical balloon (FIG. 1 and FIGS. 2A-2C).

The use of a patent specific medical balloon is made to precisely address the architecture of the blood vessel or lesion, such as a bifurcation or trifurcation lesion. Use of the patent specific medical balloon allows the physician to better respond to the positioning of wire stents. For example, an increase in diameter in the distal aspect of the balloon allows for an increase in opening of the bifurcation and ultimately to provide vessel shape that more closely resembles the normal branching of tubes to approximate normal laminar blood flow, which is less likely to provoke regrowth of tissue than turbulent flow.

Figure 2A:
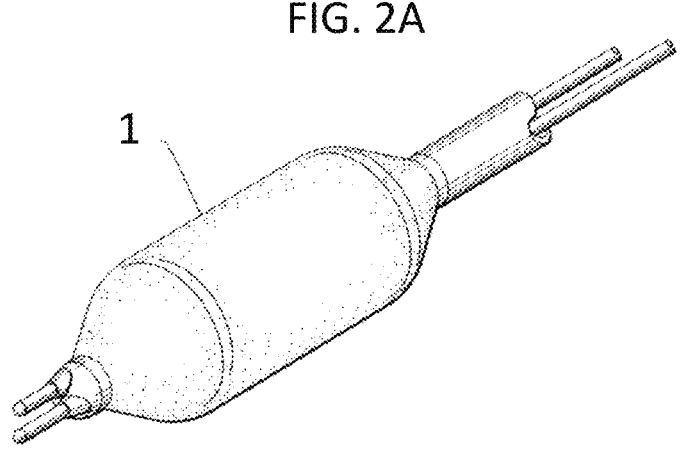
FIGS. 2A-2C illustrate distal views of dual tip catheters with uniform medical balloon (FIG. 2A), medical balloon tapered from distal to proximal (FIG. 2B), and medical balloon tapered from proximal to distal (FIG. 2C).
Figure 2B:
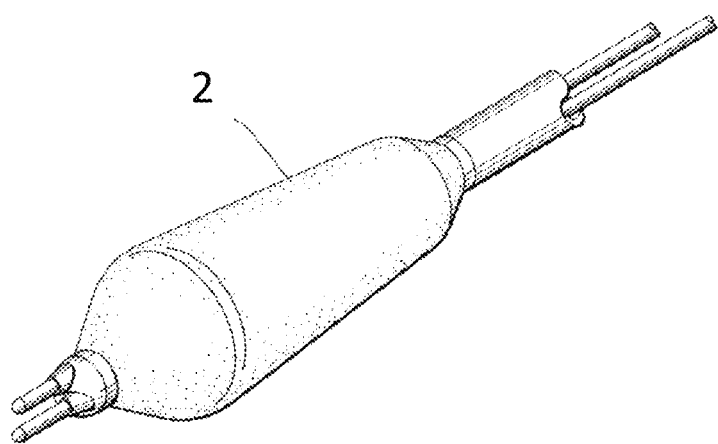
Figure 2C:
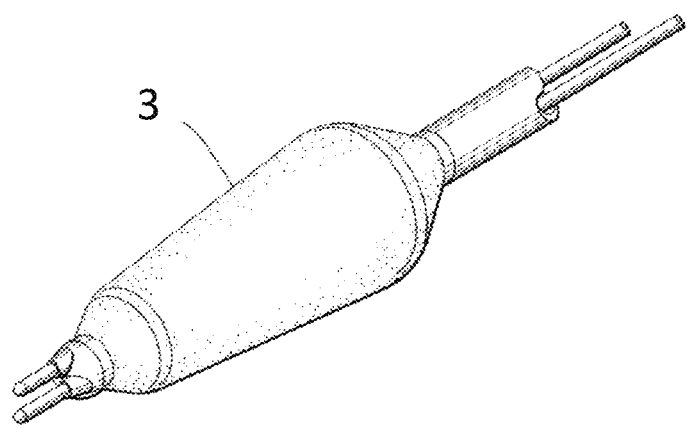

In some embodiments, the patient specific medical balloon is tapered. Suitably, the tapered medical balloon may be tapered from distal to proximal (FIG. 2B) or proximal to distal (FIG. 2C). The use of a tapered medical balloon is useful not only in conjunction with the multi-tipped catheter (FIGS. 2A-2C) but also in connection with single tip conventional wire stent and single tip catheter assembly. Using a combination of the proximally tapered medical balloon and the distally tapered medical balloon in this process may ensure the diseased area receives proper coverage by several wire stents and respects the flow characteristics surrounding a vessel bifurcation. Catheters, such as those described herein, may be prepared by attaching the patient specific medical balloons prepared by the methods described herein to a catheter suitable for use in a PCI.

Assemblies, systems, and methods of preparing patient specific medical balloons are also provided. FIG. 3 shows an exemplary assembly 10 for preparing the patient specific medical balloons as described herein. The assembly 10 comprises a form 12 for receiving a parison. The form 12 is configured to prepare a patient specific medical balloon matched in geometry to a blood vessel or lesion therein of a patient in need of a PCI in the blood vessel. The configuration of the form 12 may be determined from biometric data obtained from the subject as described further below.

Figure 4:
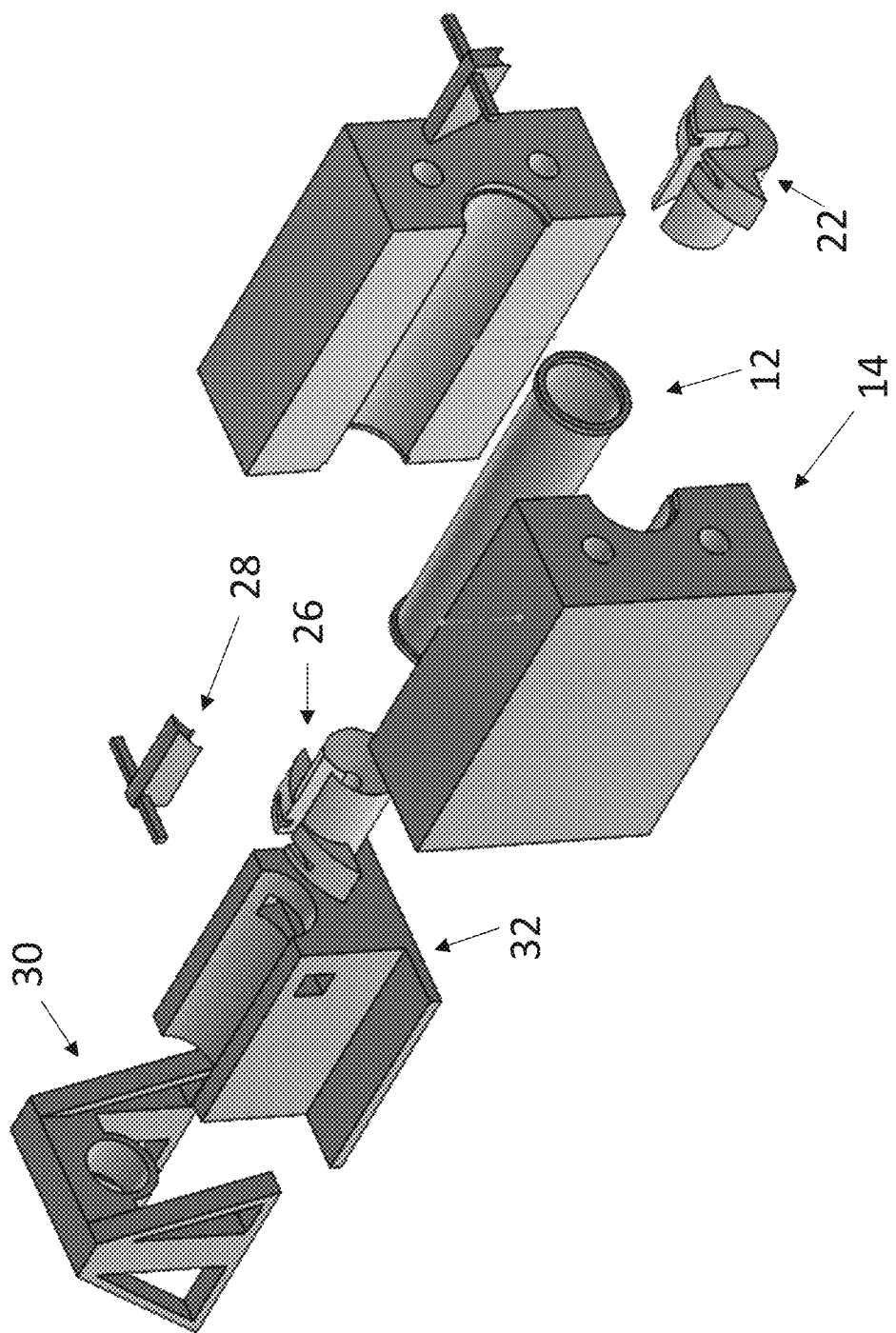
FIG. 4 illustrates an exploded view of an assembly according to the presently disclosed technology.

The form 12 may be surrounded by a heated jaw 14 and configured to heat the parison within the form 12 to a balloon forming temperature. The heated jaw may be thermally coupled to one of more heating elements 16. The heated jaw may be portioned in two as illustrated in FIG. 4. Holes may be bored into each half that allow for the insertion of heating elements 16, such as 250 W heating rods, to be placed within the heated jaw. The four rectangular faces of the heated jaw may be enveloped by insulation to limit convective air currents surrounding the heated jaw. The heated jaw may optionally be thermally coupled to one or more one internal temperature thermocouples for monitoring the temperature of the form 12 or parison. The heating element 16 may be wired to allow optimal power and controlled to allow rapid reaching of peak temperature without overshooting the temperature. In some embodiments, the heating element 16 is controlled by a controller having instructions for heating the parison to one or more balloon forming temperatures for a desired balloon forming time. The controller may also be coupled to a thermocouple for monitoring the temperature of the heated jaw 14, form 12, parison, or any combination thereof during the heating process and/or modulating the power provided to the heating element 16 based upon the monitoring.

The molds may be readily interchanged within the assembly allowing for different patient specific medical balloon to be formed. Each mold's outer dimensions may be fixed to allow for different molds to be fit within the heated jaw while the inner dimensions can be adjusted based upon the desired designs, even custom fitted for patient specific balloons. The inner dimensions may be chosen to create a tapered and mostly enclosed tubular mold.

A parison, or a pre-stretched plastic tube, will be inserted within the mold 12 and the mold 12 surrounded by the heated jaw. The parison may be heated for a desired time to a balloon forming temperature and pressurized with a balloon forming medium to expand the parison within the form 12. The parison may be heated and pressurized for a sufficient time for a patent specific medical balloon to take on the geometric parameters defined by the form 12.

A conduit 18 may be configured to provide a balloon forming medium for expanding the parison with the form. The conduit may be a lumen through a stopper 20 that is configured to provide a desired cone geometry to the proximal or distal end of the patient specific medical balloon. The stopper 20 may be clamped using a quick-release clamp that limits outward movement of the stoppers during balloon formation. The conduit 18 may be fluidly connected to a pressurizing system for pressurizing the balloon forming medium. In some configurations, the stopper 20 located between the proximal end of the balloon and the pressurizing system may be composed of two interlocking pieces 26 and 28. The pressurizing system may be held stationary with a movable stand 30 that is anchored to a permanent component 32 during balloon heating and formation using a slight interference fit. Suitably, the balloon forming medium may be selected from a gas or liquid capable of expanding the parison within the form 12. In some embodiments, a quick pressurized burst of gas or liquid is initiated which will expand the parison until it fills the mold 12. The balloon may then be depressurized, the stopper 20 removed from the mold, and newly formed balloon being pulled out from the mold 12. In some embodiments, the balloon is repressurized following removal from the mold with a quick pressurized burst of gas or liquid and depressurized once cooled. In some embodiments, the pressurizing system is controlled by a controller having instructions for pressurizing the balloon forming medium to a desired pressure for a desire balloon forming time. The controller may also be coupled to a pressure monitoring device for monitoring the pressure of the balloon forming medium during pressurization and/or modulating the pressure provided to the pressurizing system based upon the monitoring. The assembly may also include a fan or other cooling device positioned to quickly cool the balloon following removal from the heated jaw. Additionally, the cooling device may include a mechanical device to rotate the newly formed balloon during cooling. In some embodiments, the cooling system is controlled by a controller set for a desired cooling time.

The assembly also comprises a tensioning device, such as a mechanized actuator, configured apply tension to the parison within the form 12. The tensioning device may be capable of clamping down on the parison extending from the form 12 through a bore of a stopper 22 that is configured to provide a desired cone geometry to the end of the patient specific medical balloon opposite stopper 20 at position 24. The tensioning device may be used to provide tension during the balloon forming process. In some embodiments, the tensioning device is controlled by a controller having instructions for applying a balloon forming tension to the parison for a desire balloon forming time. The controller may also be coupled to a monitoring device for monitoring the tension on the parison during tensioning and/or modulating the tension provided to the tensioning device based upon the monitoring.

Methods for preparing medical balloons are described in U.S. Pat. Nos. 5,948,345, 6,946,092, and Chen Yan, Modeling and cycle-to-cycle control of the angioplasty balloon forming process (McGill University 2008), each of which are incorporated by reference in their entireties.

Systems and methods for preparing a form are also provided. The system may comprise any of the assemblies as described herein and further comprising a biometric data acquisition device, a processing device, and a forming device. The biometric data acquisition device is configured to obtain biometric information from the subject in need of the PCI of a blood vessel. Suitably the biometric data acquisition device is configured to image the blood vessel in need of PCI. In some embodiments, the blood vessel may be imaged by coronary angiography, computed tomography (CT), Micro-CT (μ-CT), optical coherence tomography (OCT), magnetic resonance imaging (MRI). ultrasound imaging (USI), X-ray imaging, positron emission tomography (PET), single-photon fluorescence microscopy (1PFM), two-photon fluorescence microscopy (2PFM), orthogonal polarization spectral imaging (OPSI), laser speckle contrast imaging (LSCI), diffuse optical tomography (DOT), photoacoustic imaging (PAI), or any combination thereof.

From the biometric data obtained from the patient, the form configured to prepare the patient specific medical balloon matched in geometry to the blood vessel or lesion of the subject in need of the PCI may be determined. A processing device may be used to determine the configuration of the form that is specific for the patent. The processing device may comprise a processor and memory storing instructions that, when executed by the processor, will cause the processing device to determine the form configured to prepare the patient specific medical balloon matched in geometry to the blood vessel. The processing device may also comprise memory storing instructions that, when executed by the processor, will cause the processing device to determine instructions for preparing the patient specific medical balloon.

After the configuration of the form is determined, the form may be created by a dedicated forming device. Suitably, the forming device may be an additive manufacturing device such as a 3D printer. The term "additive manufacturing" may refer to a variety of processes in which material is deposited, joined, or solidified under computer control to create a three-dimensional object. The material may be added together, typically layer by layer, from a variety of different materials. Additive manufacturing methodologies allow for the manufacture of patient specific form manufacturing.

Methods of forming a tapered parison are also provided. The tapered parisons prepared by the methods described herein may be used in method for forming patient specific medical balloons. In methods for treating subjects for a PCI, a patent specific medical balloon 8 mm or less in diameter, e.g., 1, 2, 3, 4, 5, 6, 7, or 8 mm in diameter, may be needed. Simply scaling the parison dimensions to a smaller diameter parison dimension can result in underinflated balloons that do not fill out the form. Under-expansion of the balloons may be due to LaPlace's law, with the smaller diameter requiring a higher pressure. Larger diameter in the parison may allow for full expansion of the balloon that filled the mold cavity, but the conical taper section of the balloons may have an undesirably thick wall thickness.

Figure 5:
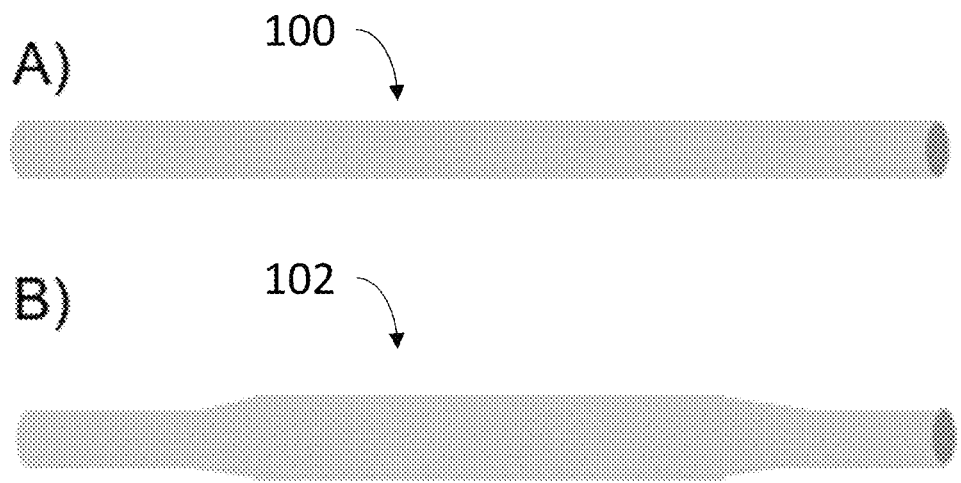
FIG. 5 illustrates parison with (A) straight walls 100 and (B) tapered walls 102.

In order to overcome the issues described above, tapered parisons can be formed and used in the balloon forming process. A tapered parison may also be referred to as a "bump" parison. FIG. 5 shows a straight walled parison 100 and a tapered parison 102 that has a intermediate portion of the parison having a larger diameter than the ends. The tapered parison 102 may be stretched to have a smaller diameter where the conical ends will form. The tapered tubing works well for creating the smaller balloons with desirable wall thicknesses and outside diameters at lower pressures than can be used with straight walled parisons.

Figure 6:
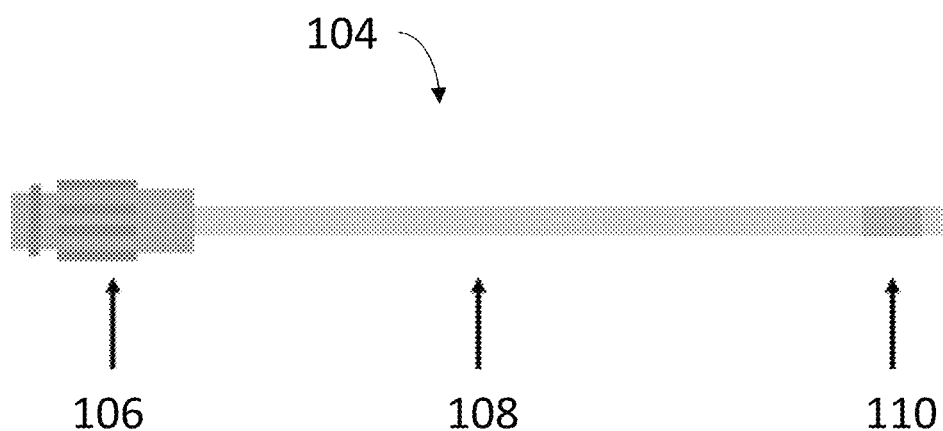
FIG. 6 illustrates a balloon parison 104 with connector 106, tubing 108, and sealed end 110.

FIG. 6 illustrates a parison 104 for use in a balloon forming method or for forming a tapered parison. The parison 104 comprises a connector 106, a sealed end 110, and tubing 108 in between the connector and sealed end. The connector 106 may be leak free connector such as a Luer Lock and the end 110 may be sealed with a glue, such as cyanoacrylate, or fused together. The tubing may be any parison material suitable for preparing a patient specific medical balloon, such as medical grade polyester (e.g., polyethylene terephthalate (PET)), polyamide, polyether block amide, and the like.

Figure 7:
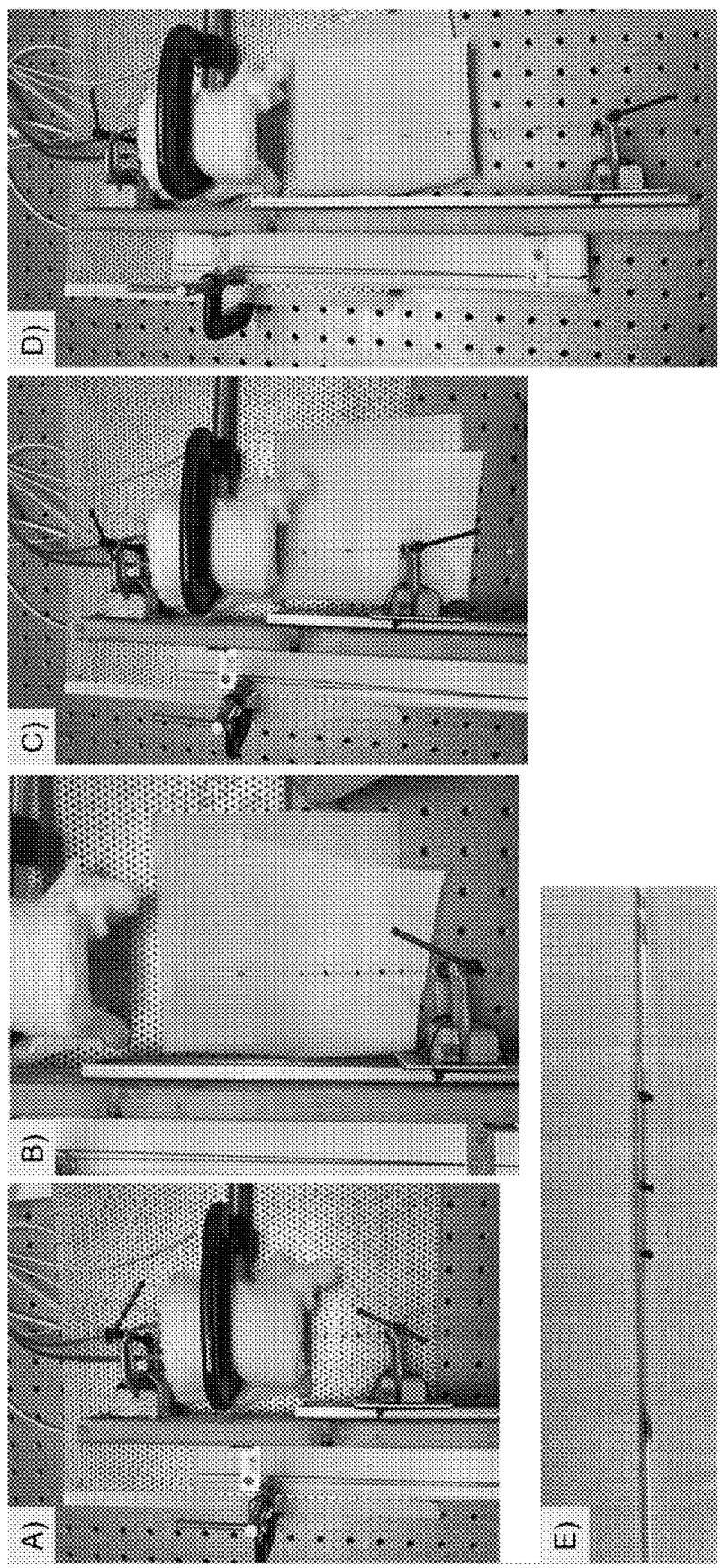
FIG. 7 illustrates a parison stretching process for forming a tapered parison: (A) shows the tubing heating in the balloon forming assembly, (B) shows the first stretch of the tubing, (C) shows the other side of the tubing being heated, and (D) shows the second stretching. Panel (E) shows the tapered tubing formed from the stretching process.

The tensioning device is an attachment to the balloon forming assembly that allows for simultaneous heating and stretching of the balloon parison material. The tensioning device may be removable. This allows for the balloon forming assembly to be used for two purposes: parison stretching and balloon forming. In some embodiments, the tensioning device is utilized to stretch parisons during balloon formation. FIG. 7 illustrates an exemplary tensioning device and its use. As shown in FIG. 7, the tensioning device comprises two clamps for coupling the ends of the parison to be stretched. One clamp may be fixed in place and the other is attached to the movable member. The movable member may be configured to move along a track or slide. In between the two clamps is the body of the balloon forming assembly, which heats a portion of the parison. The parison tubing is heated within the machine until it is malleable (FIG. 7A). In some embodiments, the parison is heated for approximately 2-4 minutes, depending on tubing wall thickness. After the tubing has reached a workable state the tensioning device is used to stretch the tubing (FIG. 7B). This may be accomplished by moving the movable member along a slid. Tension may be held while the parison cools to set the shape. The parison may be removed from the tensioning device and the position of the parison reversed (FIG. 7C) so that the other side may be stretched (FIG. 7D). The tapered parison (FIG. 7E) may be used to prepare a patient specific medical balloon.

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Embodiments of the Invention

Embodiment 1. An assembly for forming a medical balloon, the assembly comprising:
(a) a form for receiving a parison, wherein the form is configured to prepare a patient specific medical balloon matched in geometry to a blood vessel or a lesion therein of a patient in need of a percutaneous coronary intervention (PCI) in the blood vessel;
(b) a heated jaw configured to surround the form and heat the parison within the form to a balloon forming temperature, wherein the heated jaw is thermally coupled to a heating element;
(c) a conduit configured to provide a balloon forming medium for expanding the parison within the form; wherein the conduit is fluidly connected to a pressurizing system for pressurizing the balloon forming medium;
(d) a tensioning device configured to apply tension to the parison within the form; and
(e) optionally one or more controllers configured to control the heating element, the pressurizing system, or the tensioning device.

Embodiment 2. The assembly of embodiment 1, wherein the configuration of the form is determined from biometric data obtained from the subject.

Embodiment 3. The assembly of any one of embodiments 1-2, wherein the form is configured to form a tapered, patient specific medical balloon.

Embodiment 4. The assembly of any one of embodiments 1-3, wherein the PCI is an intervention for a bifurcation lesion.

Embodiment 5. The assembly of any one of embodiments 1-4, wherein the further comprises a cooling device and optionally a controller configured to control the cooling device.

Embodiment 6. A system for forming a medical balloon, the system comprising:
(a) the assembly according to any one of embodiments 1-5;
(b) a biometric data acquisition device, the biometric data acquisition device configured to obtain biometric data from the subject in need of the PCI of the blood vessel;
(c) a processing device, the processing device comprising a processor and memory storing instructions that, when executed by the processor, will cause the processing device to determine the form configured to prepare the patient specific medical balloon matched in geometry to the blood vessel or a lesion therein; and
(d) a forming device configured to form the form determined by the processing device.

Embodiment 7. The system of embodiment 6, wherein the forming device is an additive manufacturing forming device.

Embodiment 8. The system of any one of embodiments 6-7, wherein biometric data acquisition device is configured to image the blood vessel Embodiment 9. A method for preparing a form configured to prepare a patient specific medical balloon, the method comprising:
obtaining, with a biometric data acquisition device, biometric data from a subject in need of a PCI of a blood vessel;
determining, from said biometric data with a processing device, a form configured to prepare the patient specific medical balloon matched in geometry to the blood vessel or a lesion therein of the subject in need of the PCI; and
forming, with a forming apparatus, the form configured to prepare the patient specific medical balloon.

Embodiment 10. The method of embodiment 9, wherein the form is formed by an additive manufacturing process.

Embodiment 11. The method of any one of embodiments 9-10, wherein the biometric data is obtained by imaging the blood vessel.

Embodiment 12. The method of any one of embodiments 9-11, wherein the method is performed by the system according to any one of claims 6-8.

Embodiment 13. A method for forming a patient specific medical balloon, the method comprising:
  providing the assembly according to any one of embodiments 1-5;
  positioning the parison within the form; and
  expanding the parison within the form under balloon forming conditions.

Embodiment 14. The method of embodiment 13 further comprising:
  obtaining, with a biometric data acquisition device, biometric data from a subject in need of a PCI of a blood vessel;
  determining, from said biometric data with a processing device, a form configured to prepare the patient specific medical balloon matched in geometry to the blood vessel or a lesion therein of the subject in need of the PCI; and
  forming, with a forming apparatus, the form configured to prepare the patient specific medical balloon.

Embodiment 15. The method of any one of embodiments 13-14 further comprising forming a second patient specific medical balloon matched in geometry to a second blood vessel or a lesion therein of the subject suitable for use in the method for treating the subject in need of the PCI.

Embodiment 16. A method of preparing a balloon catheter device for use in a PCI, the method comprising forming a medical balloon according to any one of embodiments 13-14 and attaching the formed medical balloon to a catheter suitable for use in the PCI.

Embodiment 17. The method of embodiment 17, wherein the medical balloon is a tapered, patient specific medical balloon.

Embodiment 18. The method of any one of embodiments 16-17, wherein the PCI is an intervention for a bifurcation lesion.

Embodiment 19. A method for treating a subject in need of a percutaneous coronary intervention (PCI), the method comprising:
  locating within the subject in need of the PCI a lesion in a blood vessel having a plaque or an occlusion associated therewith;
  positioning a patient specific medical balloon matched in geometry to the blood vessel proximate to the lesion; and
  expanding the patient specific medical balloon to a matched diameter of the blood vessel to reconfigure the plaque or the occlusion within the blood vessel.

Embodiment 20. The method of embodiment 20, wherein the patient specific medical balloon is attached to a catheter.

Embodiment 21. The method of any one of embodiments 19-20, wherein the lesion is a bifurcation lesion and the patient specific medical balloon is positioned in a main branch area or distal to a carina prior to expansion.

Embodiment 22. The method of any one of embodiments 19-21 further comprising:
  positioning an expandable wire stent proximate to the reconfigured plaque or occlusion and
  expanding the expandable wire stent with the patient specific medical balloon.

Embodiment 23. A method for forming a tapered parison, the method comprising:
  providing the assembly according to any one of embodiments 1-5;
  positioning a first portion of a parison within the form and coupling a first end and a second end of the parison to the tensioning device wherein the first end extends from the form;
  heating, with the heated jaw surrounding the form, the first portion of the straight parison; tensioning, with the tensioning device, the heated parison; and
  cooling the parison under tension.

Embodiment 24. The method of embodiment 23 further comprising:
  positioning a second portion of the cooled parison within the form and coupling the first end and the second end of the parison to the tensioning device, wherein the coupling of the first end and the second end is reversed from the coupling prior to tensioning and heating;
  heating, with the heated jaw surrounding the form, the second portion of the straight parison;
  tensioning, with the tensioning device, the heated parison; and
  cooling the parison under tension.

Embodiment 25. The method of any one of embodiments 23-24, wherein the parison having the first portion positioned within the form has straight walls.

Embodiment 26. Use of the tapered parison prepared by any one of embodiments 23-25 in the method of any one of embodiments 13-18.

We claim:

1. A method for forming a tapered parison, the method comprising: providing a assembly for forming a medical balloon comprising:
  (a) a form for receiving a parison, wherein the form is configured to prepare a patient specific medical balloon matched in geometry to a blood vessel or a lesion therein of a patient in need of a percutaneous coronary intervention (PCI) in the blood vessel;
  (b) a heated jaw configured to surround the form and heat the parison within the form to a balloon forming temperature, wherein the heated jaw is thermally coupled to a heating element;
  (c) a conduit configured to provide a balloon forming medium for expanding the parison within the form; wherein the conduit is fluidly connected to a pressurizing system for pressurizing the balloon forming medium;
  (d) a tensioning device configured to apply tension to the parison within the form;
  (e) optionally one or more controllers configured to control the heating element, the pressurizing system, or the tensioning device, and
  (f) a proximal stopper and a distal stopper configured to provide a desired cone geometry to a proximal end and a distal end of the patient specific medical balloon;
  positioning a first portion of the parison within the form and coupling a first end and a second end of the parison to the tensioning device wherein the first end extends from the form;
  heating, with the heated jaw surrounding the form, the first portion of the straight parison;
  tensioning, with the tensioning device, the heated parison;
  cooling the parison under tension;
  positioning a second portion of the cooled parison within the form and coupling the first end and the second end of the parison to the tensioning device, wherein the coupling of the first end and the second end is reversed from the coupling prior to tensioning and heating;
  heating, with the heated jaw surrounding the form, the second portion of the straight parison;
  tensioning, with the tensioning device, the heated parison; and
  cooling the parison under tension.

2. The method of claim 1, wherein the proximal stopper and the distal stopper each include a clamp configured to limit an outward movement of the proximal stopper and distal stopper during formation of the patient specific medical balloon.

3. The method of claim 2, wherein the proximal stopper and the distal stopper each include a first interlocking piece and a second interlocking piece, wherein the first interlocking piece and the second interlocking piece interlock with each other.

4. The method of claim 1, wherein the configuration of the form is determined from biometric data obtained from the subject.

5. The method of claim 1, wherein the PCI is an intervention for a bifurcation lesion.

6. The method of claim 1, wherein the assembly further comprises a cooling device and optionally a controller configured to control the cooling device.

* * * * *